United States Patent [19]
Hasson

[11] Patent Number: 5,507,756
[45] Date of Patent: Apr. 16, 1996

[54] APPARATUS FOR CINCHING A KNOT ON A SURGICAL SUTURE

[76] Inventor: Harrith M. Hasson, 2551 N. Clark St., 8th Floor, Chicago, Ill. 60614

[21] Appl. No.: 327,012

[22] Filed: Oct. 21, 1994

[51] Int. Cl.⁶ ................................................. A61B 17/04
[52] U.S. Cl. ......................... 606/139; 606/148; 606/205; 606/207
[58] Field of Search ..................................... 606/113, 139, 606/144, 146, 147, 148, 205–207

[56] References Cited

U.S. PATENT DOCUMENTS

| | | | |
|---|---|---|---|
| 4,890,615 | 1/1990 | Caspri et al. | 606/145 |
| 4,935,027 | 6/1990 | Yoon | 606/146 |
| 5,318,579 | 6/1994 | Chow | 606/148 |

*Primary Examiner*—Gary Jackson
*Attorney, Agent, or Firm*—Wood, Phillips, VanSanten, Clark & Mortimer

[57] ABSTRACT

An apparatus for facilitating the tying of a knot in a flexible line that has a first portion extending through a tissue/organ and first and second free ends extending away from the first portion and wrapped around each other to thereby define a loop. The apparatus has a support to be held by a user of the apparatus, a first jaw, a second jaw, first structure cooperating between the first jaw and at least one of the support and second jaw for allowing the first jaw to be moved relative to the at least one of the support and second jaw between a) a first position wherein the first jaw and at least one of the second jaw and support cooperatively define a first annular wall bounding a space into which the flexible line can be directed along a first line and b) a second position wherein there is an entry opening defined through the first annular wall to permit entry therethrough of the flexible line into the space along a direction transverse to the first line, and second structure on at least one of the first jaw, the second jaw and support for defining a pushing surface for the flexible line in the space to allow the pushing surface to bear slidingly against the flexible line in the space to thereby cinch a knot formed in the flexible line.

20 Claims, 2 Drawing Sheets

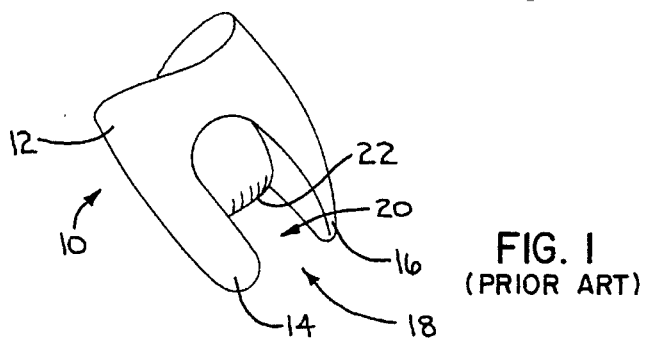
FIG. 1
(PRIOR ART)
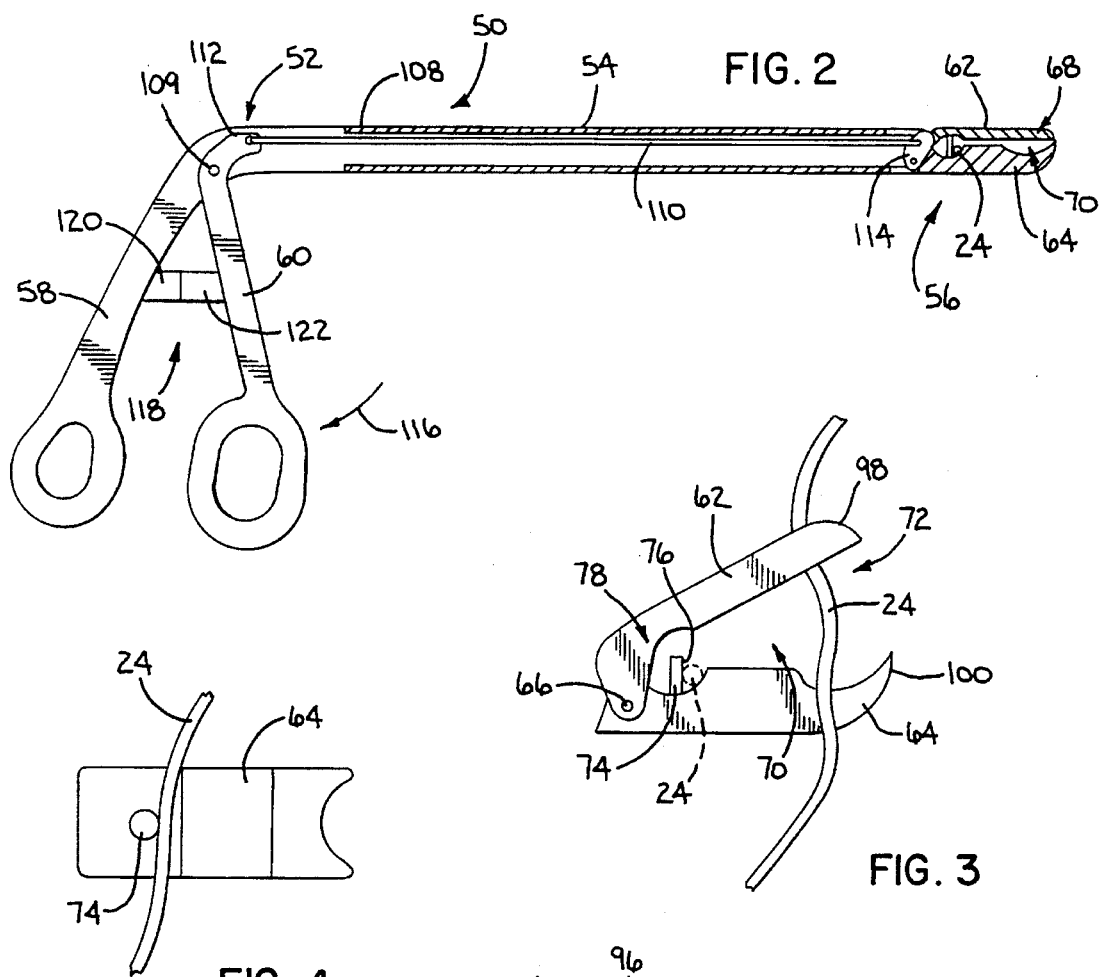
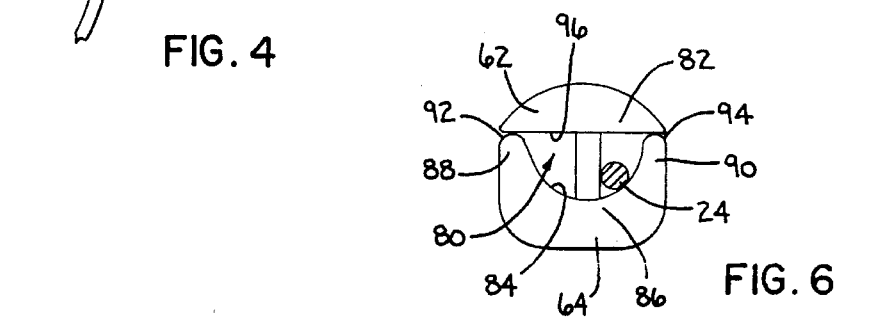

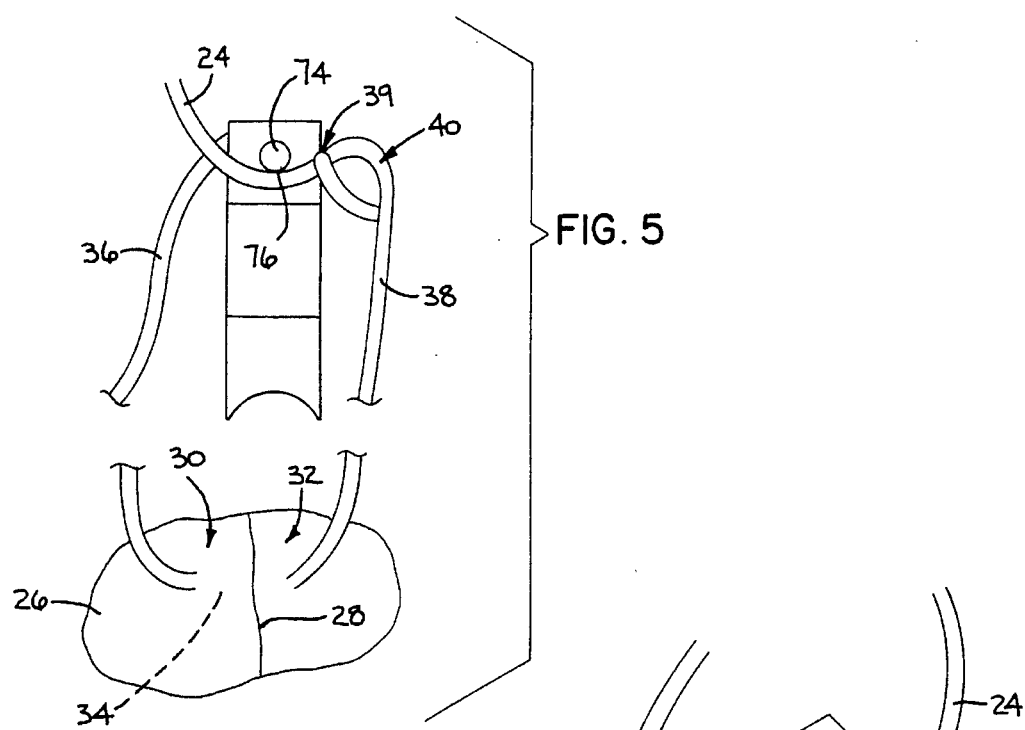
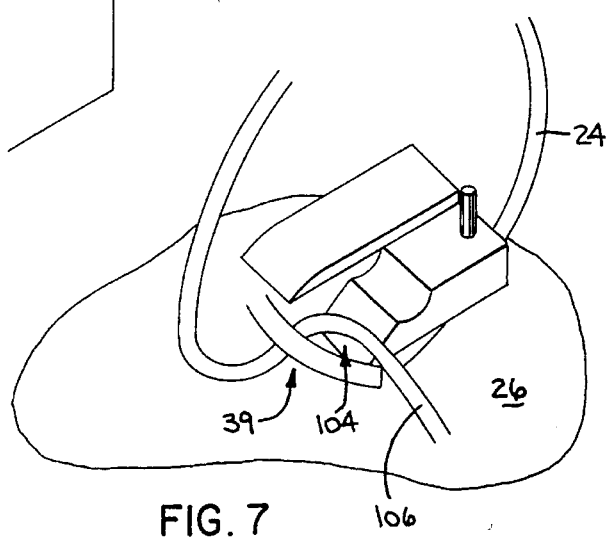
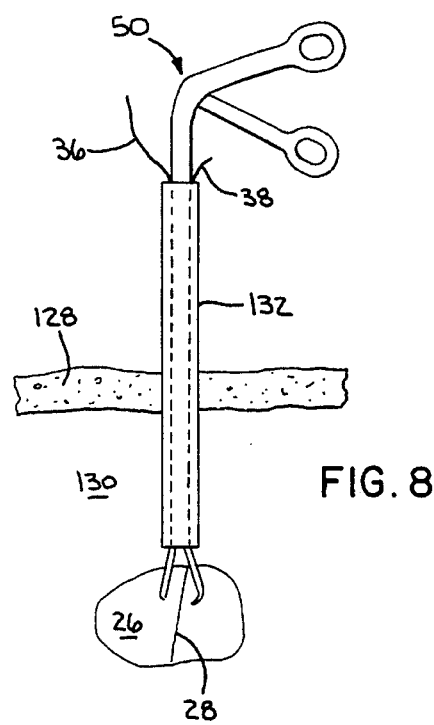
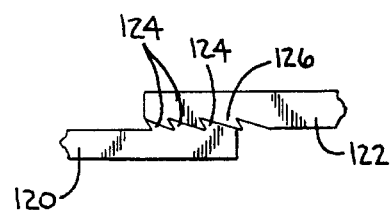

APPARATUS FOR CINCHING A KNOT ON A SURGICAL SUTURE

BACKGROUND OF THE INVENTION

1. Field of the Invention

This invention relates to surgical suturing and, more particularly, to an apparatus that facilitates the cinching of a knot in the suture, as from externally of a cavity in which a laparoscopic procedure is performed. The invention is also directed to a method of cinching a knot utilizing the apparatus.

2. Background Art

Suturing tissue in an open body cavity is a relatively tedious and delicate procedure. This is due principally to the thinness of the suturing thread as well as its tendency to twist about its length. In a normal suturing procedure, the thread is directed through a tissue and the free ends thereof are wrapped to define a half-hitch knot that froths a closed loop, the diameter of which can be reduced ultimately to the point that the thread is cinched at the tissue. As twisting of the thread occurs, restriction of the loop is inhibited, possibly to the point that it is impossible to cinch the knot at the body tissue, as required. Even after one half-hitch knot is formed and properly cinched, the twisting problem persists and may interfere with, or prevent, the subsequent formation of additional half-hitch knots as would "lock" the suture. When this occurs, the surgeon may be required to cut the suture and re-start the process. This process is by nature time consuming. These problems increase the overall time of the operation and contribute undesirably to hand, and overall, surgeon fatigue.

It is known to suture during laparoscopy internally of a cavity. The problems attendant the conventional open procedure described above are present. In fact, these problems are aggravated by reason of having to handle the suturing thread almost completely through the use of elongate instruments. The surgeon is required to extend at least two instruments into the operative cavity and to watch the procedure through a monitor that employs optical fibers extended into the cavity. This type of suturing process may be time consuming and frustrating to the surgeon, particularly in those instances when partially, or improperly formed sutures, must be cut and removed from the cavity.

To effect removal of an improperly tied suture, the surgeon is generally required to direct a separate instrument into the cavity through a cannula. This instrument may be either one that permits grasping of the suture to effect untying thereof, such as a forceps, or a cutting instrument. The use of a forceps to untie a fully or partially formed knot is inconvenient. It is difficult to grasp and hold the thread at a desired location to effect manipulation thereof. This is a particularly difficult task with a tangled or twisted thread.

It is also known to form a half-hitch knot on a suture from a location externally of the tissue. This method, known as extra-corporeal suturing, involves the step of directing a suture carrying needle through a cannula, through internal body tissue, and out the proximal end of the cannula so that the free ends of the suturing thread are accessible from externally of the cavity. The surgeon then manipulates the free ends of the suturing thread by wrapping the threads in such a manner as to define a half-hitch knot. An elongate "pusher" rod, with a bifurcated free end, is engaged with one of the free ends of the thread in the vicinity of where they are wrapped and pressed through the cannula, while at the same time holding both free thread ends projecting away from the loop. As this takes place, the loop diameter restricts to the point that it is ultimately cinched at the tissue.

This procedure is convenient from the standpoint that the half-hitch knots can be formed from externally of the body cavity. However, this introduces other complications. The problem of thread tangling persists. Further, the procedure is inherently awkward by requiring that the free ends of the suture projecting away from the loop be held taut as a pusher is pressed through the cannula to reduce the loop diameter. Thus, there are three manipulation points - the two free ends of the thread projecting away from the loop must be held and one of the threads at the wrapped portion of the loop must be pressed through the cannula. The result is that the procedure may require two sets of hands.

Further, the thread is prone to escaping from the open free end of the pusher. When this occurs, the surgeon is required to attempt to reposition the thread in the pusher end. This is a difficult and time consuming procedure that may be made impossible by twisting of the thread that occurs within the cavity. The end result of this may be that the surgeon may be required to remove the partially locked suture and re-start the procedure.

Further, since the thread is prone to twisting, the thread may bind as the loop diameter is restricted. Excessive pressure exerted by the pusher on the thread with this condition may result in thread breakage.

SUMMARY OF THE INVENTION

In one form of the invention, an apparatus is provided for facilitating the tying of a knot in a flexible line that has a first portion extending through a tissue/organ and first and second free ends extending away from the first portion and wrapped around each other to thereby define a loop. The apparatus has a support to be held by a user of the apparatus, a first jaw, a second jaw, first structure cooperating between the first jaw and at least one of the support and second jaw for allowing the first jaw to be moved relative to the at least one of the support and second jaw between a) a first position wherein the first jaw and at least one of the second jaw and support cooperatively define a first annular wall bounding a space into which the flexible line can be directed along a first line and b) a second position wherein there is an entry opening defined through the first annular wall to permit entry therethrough of the flexible line into the space along a direction transverse to the first line, and second structure on at least one of the first jaw, the second jaw and support for defining a pushing surface for the flexible line in the space to allow the pushing surface to bear slidingly against the flexible line in the space to thereby cinch a knot formed in the flexible line.

The invention further contemplates the combination of the apparatus with a flexible line. The space defined by the first annular wall has a first effective diameter. The diameter of the flexible line is preferably substantially less than the first effective diameter.

With the flexible line in an operative position between the jaws, the knot can be pushed to the desired destination without twisting or entanglement of the line, and without the fear of separation of the line from the apparatus.

In one form, the first cooperating structure is structure for connecting the first jaw to the at least one of the support and second jaw for pivoting movement relative thereto about a first pivot axis.

The annular space has a central axis that in one form is substantially parallel to the first pivot axis. The central axis may be transverse to the first pivot axis and in one form the central axis is at a right angle to the first pivot axis.

At least one of the first and second jaws has a U-shaped surface and with the first jaw in the first position the U-shaped surface and the other of the first and second jaws cooperatively define a second annular wall bounding a second space that is in communication with the space bounded by the first annular wall.

At least one of the first and second jaws may have a free end with a sharp tooth thereon that can be used to untie a knot in the flexible line.

In one form, the U-shaped surface has a base and first and second legs each having a free end and at least one of the first and second legs has a sharpened free end to facilitate movement of the free end of the one of the first and second legs into a space between wrapped portions of the flexible line to facilitate manipulation thereof, i.e. loosening or untying.

With the first jaw in the first position, the first jaw bridges the free ends of the first and second legs.

The second structure may include a crowed surface.

In one form, the second structure is an elongate post, with the length of the post extending transversely to the first pivot axis. The length of the post may be at substantially a right angle to the first pivot axis.

The support may include a third structure thereon for moving the first jaw selectively between the first position and the second position from a location remote from the first jaw.

The support may be elongate with proximal and distal ends and include first and second grips at the proximal end, with the first and second jaws being provided at the distal end of the support.

The third structure may include an elongate rod with spaced ends, with structure for connecting one end of the elongate rod to one of the first and second grips, structure for connecting the other end of the elongate rod to the first jaw, and structure for connecting the one of the first and second grips to the other of the first and second grips for movement between a) a first position wherein the first grip causes the elongate rod to be repositioned so as to move the first jaw into its first position and b) a second position wherein the first grip causes the elongate rod to be repositioned so as to move the first jaw into its second position.

The invention further contemplates a method of cinching a knot formed in a flexible line that has a first portion extending through a tissue/organ and first and second free ends projecting away from the first portion and wrapped around each other to form a knot which defines a loop. The method includes the steps of: providing an apparatus having a support, a first jaw, a second jaw, and first structure cooperating between the first jaw and at least one of the support and second jaw for allowing the first jaw to be moved relative to the at least one of the support and second jaw between a) a first position wherein the first jaw and at least one of the second jaw and support cooperatively define a first annular wall bounding a space into which the flexible line can be directed along a first line and b) a second position wherein there is an entry opening defined through the first annular wall to permit ennui therethrough of the flexible line into the space transversely to the first line; placing the first jaw in the second position; directing one of the free ends of the flexible line through the entry opening through the first annular wall; placing the first jaw in the first position; and sliding the first and second jaws along one of the free ends of the flexible line towards the first portion of the flexible line to thereby reduce the diameter of the loop.

The invention further contemplates the steps of placing the first jaw in the second position after sliding the first and second jaws along the one of the free ends of the flexible line and separating the apparatus from the flexible line.

The one of the first and second jaws may have a free end with a sharp tooth thereon. The method may include the step of using the sharp tooth to engage one of the free ends of the flexible line to facilitate manipulation thereof.

The invention may further include the step of locking the first jaw in at least one of the first and second positions.

BRIEF DESCRIPTION OF THE DRAWINGS

FIG. 1 is a fragmentary perspective view of the end of a conventional pusher rod used to cinch a knot in a suture;

FIG. 2 is a side elevation view of an apparatus for facilitating the tying of a knot in a suture, according to the present invention, and shown partially in cross section and with cooperating jaws thereon in a closed state;

FIG. 3 is an enlarged, side elevation view of the jaws on the apparatus in FIG. 2, with the jaws in an open state and a flexible line directed through an entry opening therebetween into a first operative position with a space between the jaws;

FIG. 4 is an enlarged, plan view of the bottom jaw with a thread in the first operative position to be pushed by the apparatus;

FIG. 5 is an enlarged, plan view of the lower jaw as in FIG. 4 and showing a line in the first operative position being pushed to cinch a knot;

FIG. 6 is an enlarged, front elevation view of the first and second jaws in a closed state and with a flexible line directed therethrough in a second operative position;

FIG. 7 is an enlarged, fragmentary, perspective view of the jaws in an open state and with a tooth on the lower jaw being used to engage the flexible line and untie a knot therein;

FIG. 8 is a reduced, side elevation view showing the inventive apparatus being extended through a cannula through tissue and into a cavity in which a suturing procedure is earned out; and FIG. 9 is an enlarged, fragmentary, plan view of structure for locking the jaws in the closed state.

DETAILED DESCRIPTION OF THE DRAWINGS

In FIG. 1, the distal end of a conventional pusher rod is shown at 10. The pusher rod 10 has an elongate body 12. The distal end thereof is bifurcated to define spaced legs 14, 16 between which an entry opening 18 to a line holding space 20 is defined. The line holding space 20 is bounded by a curved surface 22 which is used to bear slidingly against a flexible line 24, shown in FIG. 5, to cinch a knot formed therein.

More particularly, with reference to FIG. 5, the flexible line 24 is used to form a suture in a tissue/organ 26, as to close an incision 28 therein. The line 24 is directed into the tissue/organ 26 on one side 30 of the incision 28 and outwardly through the tissue/organ 26 at the other side 32 of the incision 28. A portion 34 of the flexible line 24 extends through the tissue/organ 26 and has free ends 36, 38 which extend away from the portion 34 and are wrapped around each other to form a half-hitch knot 39 that defines a closed loop 40.

Once the loop 40 is formed, it can be reduced in diameter by holding the free ends 36, 38 and pressing on one of the free ends 36, 38 at, in this case, the half-hitch knot 39. By pressing one of the free ends 36, 38 towards the line portion 34, the loop 40 is restricted in diameter and ultimately cinched at the tissue/organ 26.

This cinching is conventionally carried out using the pusher 10. One of the free ends 36, 38 of the flexible line 24 at the knot 39 is directed through the entity opening 18 into the space 20 and against the curved bearing surface 22. The surface 22 can be used to continuously urge the one free end 36, 38 downwardly towards the line portion 34. The only thing that keeps the line 24 from escaping from the space 20 is the urging of the surface 22 against the line 24 by the user during the procedure. However, it is common for the line 24 to escape from the space 20, in which event the user is required to either attempt to resituate the line 24 in the space 20 or untie the knot and re-start the tying procedure.

This latter procedure is particularly difficult in light of the fact that the line 24, in suturing operations, is thin and prone to twisting. It is difficult using a conventional forceps to grasp the knotted line in an appropriate position to effect untying thereof.

According to the invention, an apparatus is provided at 50, as shown in FIGS. 2–9, for facilitating the cinching and untying of a knot in the flexible line 24. The apparatus 50 has an elongate support 52 to be held by a user of the apparatus. The support 52 includes an elongate body 54 with a working head 56 at its distal end and first and second grips 58, 60 at its proximal end to facilitate grasping of the instrument and operation of the working head 56.

More particularly, the working head 56 includes a first jaw 62 and a second jaw 64 connected by a pin 66 for relative pivoting movement about a laterally extending axis between the closed position, shown in FIG. 2, and the open position, shown in FIG. 3. In this case, the jaw 64 is shown to be stationary with the body 54. The second jaw 62 is shown to be pivoted to the first jaw 64. It should be understood that the working head 56 could be a double-acting jaw, wherein the second jaw 64 also pivots relative to the first jaw 62 and the body 54. The jaws 62, 64 could each be pivoted to each other and/or to the body 54.

With the first jaw 62 in the closed position, the first and second jaws cooperatively define an annular wall 68 that completely bounds a laterally opening space 70 into which the line 24 can be directed.

The length of the line 24 can be directed laterally into the space 70 either by opening the first jaw 62 to define an entry opening 72 pass the wall 68 or by threading the line 24 laterally through the space 70 parallel to the center axis of the space 70 with the first jaw 62 closed.

A cylindrical post 74 is fixedly mounted on, in this case, the second jaw 64 at the rear of the space 70 and defines a curved, line bearing surface 76, corresponding to the surface 22 in the prior art pusher rod 10. The post 74 is located forwardly sufficiently to prevent the line 24 in the space 70 from contacting the meshing portions of the jaws 62, 64 at 78. The jaws 62, 64 at the meshing portions 78 move in a scissors-like action that could sever the line 24 in the absence of the post 74. Additionally, the jaws 62, 64 may have sharp edges at the meshing portions 78 which could also cause severance of the line 24. With the line 24 seated against the post 74, as shown in phantom lines in FIG. 3, the line 24 is consistently pressed only against the rounded surface on the post 74.

With the free ends 36, 38 formed into a knot 40 as shown in FIG. 5, and one of the free ends 36, 38 borne against the bearing surface 76 on the post 74, the diameter of the loop 40 can be restricted by pressing the one of the free ends 36, 38 towards the line portion 34 until cinching occurs. So long as the jaws 62, 64 remain closed, the laterally directed line 24 cannot escape from therebetween. Thus the surgeon can allow the line 24 to slacken without fear of having to re-grip the line 24 during the cinching step.

The apparatus shown has a second space 80 at the distal end thereof bounded by a wall surface defined cooperatively by a forward portion 82 of the first jaw 62 and a U-shaped forward surface 84 on the jaw 64.

The surface 84 has a base 86 and first and second, laterally spaced legs/teeth 88, 90, each of which tapers upwardly to a sharp point 92, 94 at the free ends thereof. The points 92, 94 are bridged by a flat, underside surface 96 of the first jaw 62 to enclose the space 80. With the jaw 62 open, an entry opening is defined between the jaws to allow placement of the line 24 in the space 80 as shown in FIG. 6.

With the line in the operative position of FIG. 6, the apparatus 50 can be slid lengthwise of the line 24 to cinch the knot 40. The forwardmost portions 98, 100 of the jaws 62, 64, respectively, are curved to provide a blunt surface that will allow the knot 40 to be tightly cinched without severing the line 24 or damaging the tissue/organ 26.

The jaw 64 can also be used to untie a knot as shown at 102 in FIG. 7. By opening the jaw 62, the points 92, 94 on the teeth 88, 90 are exposed and can be slipped as shown in FIG. 7 into the space at 104 between the turns of the knot 39 to allow the thread portion 106 to be pried upwardly.

The support 52 is constructed to allow actuation of the jaw 62 from a location remote therefrom. In this particular version, the body 54 has a main, cylindrical section 108 which is rigidly formed with, and terminates at, the grip 58. The grip 60 is mounted on the grip 58 by a pin 109 to allow the grip 60 to pivot relative to the grip 58 and body 54 about a laterally extending axis.

An elongate rod 110 pivotably connects between an offset leg 112 on the grip 60 and an offset leg 114 on the jaw 62. Pivoting movement of the grip 60 in the direction of the arrow 116 causes the rod 110 to be advanced forwardly to thereby pivot the jaw 62 in a clockwise position about the pin 66 into the closed position of FIG. 2.

Means is provided at 118 to lock the jaw 62 in the closed position. The means 118 includes a toothed tab 120 on the grip 58 and a cooperating toothed tab 122 on the grip 60. As the grip 60 is moved in the direction of the arrow 116, the teeth 124, 126 on the tab 120, 122, respectively, progressively intermesh to allow the progressively increasing gripping force between the jaws 62, 64 to be maintained. The means 118 is released by drawing the grip 60 in the direction of arrow 116 and shifting the grip 60 slightly laterally to allow the tabs 120, 122 to be moved past each other without interference.

In a typical procedure, the apparatus 50 is directed through a tissue 128 into a cavity 130 in which the tissue/organ 26 resides. This is facilitated by first directing a cannula 132 through the tissue 128 and into the cavity 130 in close proximity to the tissue/organ 26. The free ends 36, 38 of the line 24 can be exposed at the proximal end of the cannula 132 and wrapped to define a half-hitch knot, whereupon the loop 39 defined by the knot 39 can be reduced in diameter by directing the working head 56, with the line 24 in the space 70, or space 80, through the cannula 132 into close proximity to the tissue/organ 26.

Since each of the spaces 70, 80 has an effective diameter that is significantly greater than that of the line 24, the line 24 can be easily and conveniently grasped between the jaws 62, 64. At the same time, the line 24 is prohibited from escaping from its operative position between the jaws 62, 64 by reason of the spaces 70, 80 being completely bounded with the jaws 62, 64 closed.

The locking means 118 obviates the need to have to maintain a closing force on the grips 58, 60. The surgeon need then concentrate only on shifting the knot 39, without fear of line twisting or escape.

The apparatus 50, in addition to being more reliable in use than the conventional pusher rod 10, is more versatile, allowing loosening of a knot with the same instrument used to cinch the knot, thereby obviating the need to remove and insert different instruments.

The apparatus 50 can be reused and sterilized using an autoclave.

The foregoing disclosure of specific embodiments is intended to be illustrative of the broad concepts comprehended by the invention.

I claim:

1. An apparatus for facilitating the tying of a knot in a flexible line that has a first portion extending through a tissue/organ and first and second free ends extending away from the first portion and wrapped around each other to define a loop, said apparatus comprising:

a support to be held by a user of the apparatus;

a first jaw;

a second jaw;

first means located between the first jaw and at least one of the support and second jaw for allowing the first jaw to be moved relative to the at least one of the support and second jaw between a) a first position wherein the first jaw and at least one of the second jaw and support cooperatively define a first annular wall bounding a space within which the flexible line is adapted to be directed along a first line and b) a second position wherein there is an entry opening defined through the first annular wall to permit entry therethrough of the flexible line into the space transversely to the first line; and second means on at least one of the first jaw, the second jaw and support for defining a pushing surface for the flexible line in the space to allow the pushing surface to bear slidingly against a flexible line in the space to thereby cinch a knot formed in the flexible line.

2. The apparatus for facilitating the tying of a knot in a flexible line according to claim 1 wherein the space has a first effective diameter and further in combination with a flexible line having a diameter that is substantially less than the first effective diameter.

3. The apparatus for facilitating the tying of a knot in a flexible line according to claim 1 wherein one of the first and second jaws has a U-shaped surface and with the first jaw in the first position, the U-shaped surface and the other of the first and second jaws cooperatively define a second annular wall in communication with the space.

4. The apparatus for facilitating the tying of a knot in a flexible line according to claim 3 wherein the U-shaped surface has a base and first and second legs each having a free end and at least one of the first and second legs has a sharpened free end to facilitate movement of the free end of the one of the first and second legs into a space between wrapped portions of the flexible line to facilitate untying of a knot in the flexible line.

5. The apparatus for facilitating the tying of a knot in a flexible line according to claim 1 wherein at least one of the first and second jaws has a free end with a sharp tooth thereon that can be used to untie a knot in the flexible line.

6. The apparatus for facilitating the tying of a knot in a flexible line according to claim 1 wherein the U-shaped surface has a base and first and second legs each having a free end and with the first jaw in the first position the first jaw bridges the free ends of the first and second legs.

7. The apparatus for facilitating the tying of a knot in a flexible line according to claim 1 wherein the second means comprises a curved surface.

8. The apparatus for facilitating the tying of a knot in a flexible line according to claim 1 wherein the support includes third means thereon for moving the first jaw selectively between its first position and second positions from a location remote from the first jaw.

9. The apparatus for facilitating the tying of a knot in a flexible line according to claim 8 wherein the support is elongate and has a proximal end and a distal end, the support includes first and second grips at the proximal end of the support and the first and second jaws are at the distal end of the support.

10. The apparatus for facilitating the tying of a knot in a flexible line according to claim 9 where the third means comprises an elongate rod with spaced ends, means for connecting one end of the elongate rod to one of the first and second grips, means for connecting the other end of the elongate rod to the first jaw, and means for connecting one of the first and second grips to the other of the first and second grips for movement between a) a first position wherein the first grip causes the elongate rod to be repositioned so as to move the first jaw into its first position and b) a second position wherein the first grip causes the elongate rod to be repositioned so as to move the first jaw into its second position.

11. The apparatus for facilitating the tying of a knot in a flexible line according to claim 1 wherein the first cooperating means comprises means for connecting the first jaw to the at least one of the support and second jaw for pivoting movement relative thereto about a first pivot axis.

12. The apparatus for facilitating the tying of a knot in a flexible line according to claim 11 wherein the annular space has a central axis that is transverse to the first pivot axis.

13. The apparatus for facilitating the tying of a knot in a flexible line according to claim 12 wherein the annular space has a central axis that is substantially at a right angle to the first pivot axis.

14. The apparatus for facilitating the tying of a knot in a flexible line according to claim 11 wherein the second means comprises an elongate post and the length of the post extends transversely to the first pivot axis.

15. The apparatus for facilitating the tying of a knot in a flexible line according to claim 14 wherein the length of the post is at substantially a right angle to the first pivot axis.

16. The apparatus for facilitating the tying of a knot in a flexible line according to claim 11 wherein the annular space has a central axis that is substantially parallel to the first pivot axis.

17. A method of cinching a knot formed in a flexible line that has a first portion extending through a tissue/organ and first and second free ends projecting away from the first portion and wrapped around each other to form a knot which defines a loop, said method comprising the steps of:

providing an apparatus having a support, a first jaw, a second jaw, and first means cooperating between the first jaw and at least one of the support and second jaws for allowing the first jaw to be moved relative to the at least one of the support and second jaw between a) a first position wherein the first jaw and at least one of the second jaw and support cooperatively define a first annular wall bounding a space within which the flexible line can be directed along a first line and b) a second position wherein there is an entry opening defined through the first annular wall to permit entry therethrough of the flexible line into the space transversely to the first line;

placing the first jaw in the second position;

directing one of the free ends of the flexible line through the entry opening through the first annular wall;

placing the first jaw in the first position; and sliding the first and second jaws along the one of the free ends of the flexible line towards the first portion of the flexible line to thereby reduce the diameter of the loop.

18. The method of cinching a knot formed in a flexible line according to claim 17 including the step of placing the first jaw in the second position after sliding the first and second jaws along the one of the free ends of the flexible line and separating the apparatus from the flexible line.

19. The method of cinching a knot formed in a flexible line according to claim 17 wherein one of the first and second jaws has a free end with a sharp tooth thereon and including the step of using the shape tooth to engage one of the free ends of the flexible line to facilitate manipulation thereof.

20. The method of cinching a knot formed in a flexible line according to claim 17 including the step of locking the first jaw in at least one of the first and second positions.

* * * * *